US009302064B2

(12) United States Patent
Hussain

(10) Patent No.: US 9,302,064 B2
(45) Date of Patent: Apr. 5, 2016

(54) OXYGEN FACE MASK WITH CAPNOMETER AND SIDE PORT

(71) Applicant: Shabina M Hussain, Great Neck, NY (US)

(72) Inventor: Shabina M Hussain, Great Neck, NY (US)

( * ) Notice: Subject to any disclaimer, the term of this patent is extended or adjusted under 35 U.S.C. 154(b) by 618 days.

(21) Appl. No.: 13/654,394

(22) Filed: Oct. 17, 2012

(65) Prior Publication Data

US 2014/0107517 A1 Apr. 17, 2014

(51) Int. Cl.

| | |
|---|---|
| ***A62B 18/02*** | (2006.01) |
| ***A61M 16/06*** | (2006.01) |
| ***A61B 5/097*** | (2006.01) |
| *A61M 16/00* | (2006.01) |
| *A61M 16/10* | (2006.01) |
| *A61M 16/08* | (2006.01) |
| *A61B 5/00* | (2006.01) |

(52) U.S. Cl.

CPC ............ *A61M 16/0672* (2014.02); *A61B 5/097* (2013.01); *A61M 16/06* (2013.01); *A61B 5/682* (2013.01); *A61B 5/6819* (2013.01); *A61M 16/0078* (2013.01); *A61M 16/0683* (2013.01); *A61M 16/085* (2014.02); *A61M 16/0833* (2014.02); *A61M 16/10* (2013.01); *A61M 2202/0208* (2013.01); *A61M 2230/432* (2013.01)

(58) Field of Classification Search

CPC ........... A61M 16/06; A61M 16/0666; A61M 16/085; A61M 16/0683; A61B 5/097

USPC ....................................... 128/206.21, 206.28

See application file for complete search history.

(56) References Cited

U.S. PATENT DOCUMENTS

| | | | | |
|---|---|---|---|---|
| 4,328,797 A * | 5/1982 | Rollins, III | A61M 16/06 128/202.15 |
| 5,005,571 A * | 4/1991 | Dietz | A61M 16/06 128/205.25 |
| 7,861,718 B2 * | 1/2011 | Janbakhsh et al. | 128/205.25 |
| 2003/0024533 A1 * | 2/2003 | Sniadach | 128/205.25 |
| 2003/0168063 A1 * | 9/2003 | Gambone et al. | 128/203.16 |
| 2008/0142019 A1 * | 6/2008 | Lewis et al. | 128/207.18 |
| 2013/0172768 A1 * | 7/2013 | Lehman | 600/532 |

* cited by examiner

*Primary Examiner* — Kristen Matter

(74) *Attorney, Agent, or Firm* — Lyman Smith

(57) ABSTRACT

A nasal cannula allows insertion of an upper endoscopy probe, a transesophageal echo probe for exams, or the like. Currently, a nasal cannula is used to measure expired carbon dioxide and deliver oxygen to sedated patients undergoing these procedures. Use of a face mask, such as a non-rebreathing face mask, during these procedures allows increased delivery of oxygen in patients with compromised respiratory function. A side port can be cut into the non-rebreathing face mask to allow insertion of the probes into patient's mouths while allowing delivery of a higher oxygen concentration. The facemask has the ability to easily separate from the nasal cannula, providing for continued use of the nasal cannula during, for example, a recovery period from sedation.

12 Claims, 3 Drawing Sheets

14
28
32
40
32
38
24
18

OXYGEN FACE MASK WITH CAPNOMETER AND SIDE PORT

BACKGROUND OF THE INVENTION

The present invention relates to oxygen face masks and, more particularly, to an oxygen face mask with capnometer and side port for use in sedated patients undergoing endoscopy or transesophageal echocardiograms.

Oxygen delivery by nasal cannula allows insertion of upper endoscopy probes and transesophageal probes into the mouth. Patients undergoing an upper endoscopy or transesophageal echocardiogram need to be sedated. Sedated patients require supplemental oxygen. Currently, supplemental oxygen is delivered using a nasal cannula. This method of oxygen delivery is inadequate for patients with compromised pulmonary function, obesity and/or sleep apnea because the oxygen saturation drops, requiring probe withdrawal and subsequent rescue ventilation with a bag-valve (AMBU) mask. This can result in having to interrupt the sedation and/or the procedure.

Oxygen delivered by a non-rebreathing face mask is higher than a nasal cannula. However the non-rebreathing face mask covers the mouth.

As can be seen, there is a need for an improved oxygen face mask that allows high concentration oxygen delivery in a sedated patient undergoing upper endoscopy or transesophageal echocardiograms.

SUMMARY OF THE INVENTION

In one aspect of the present invention, an oxygen delivery device comprises a face mask adapted to fit over a nose and mouth of a patient; a side port formed in a side portion of the face mask; and a nasal cannula disposed in the face mask, the nasal cannula having prongs disposed into the nose of the patient under the face mask. The face mask having a slit at the insertion site of the nasal cannula for removal of the face mask from the nasal cannula at the end of the procedure.

In another aspect of the present invention, an oxygen delivery device comprises a face mask adapted to fit over a nose and mouth of a patient; an oxygen reservoir bag operable to release oxygen into the face mask; a tube side port formed in a side portion of the face mask; a nasal cannula disposed in the face mask, the nasal cannula having prongs disposed into the nose of the patient under the face mask; and a strap passing through strap holes in each side of the face mask, the strap operable to support the face mask on the patient, the strap adjustably attaching to itself with and hook- and loop-fastener.

In a further aspect of the present invention, an oxygen delivery device comprises a face mask adapted to fit over a nose and mouth of a patient; an oxygen reservoir bag operable to release oxygen into the face mask; an oxygen input tube operable to deliver oxygen to the face mask and the oxygen reservoir bag; a tube side port formed in a side portion of the face mask, the side port allowing an endoscopy tube to be used in the patient while the face mask is disposed on the patient; a nasal cannula disposed in the face mask, the nasal cannula having prongs disposed into the nose of the patient under the face mask; and a strap passing through strap holes in each side of the face mask, the strap operable to support the face mask on the patient, the strap adjustably attaching to itself with a hook and loop fastener.

These and other features, aspects and advantages of the present invention will become better understood with reference to the following drawings, description and claims.

DETAILED DESCRIPTION OF THE INVENTION

Figure 1:
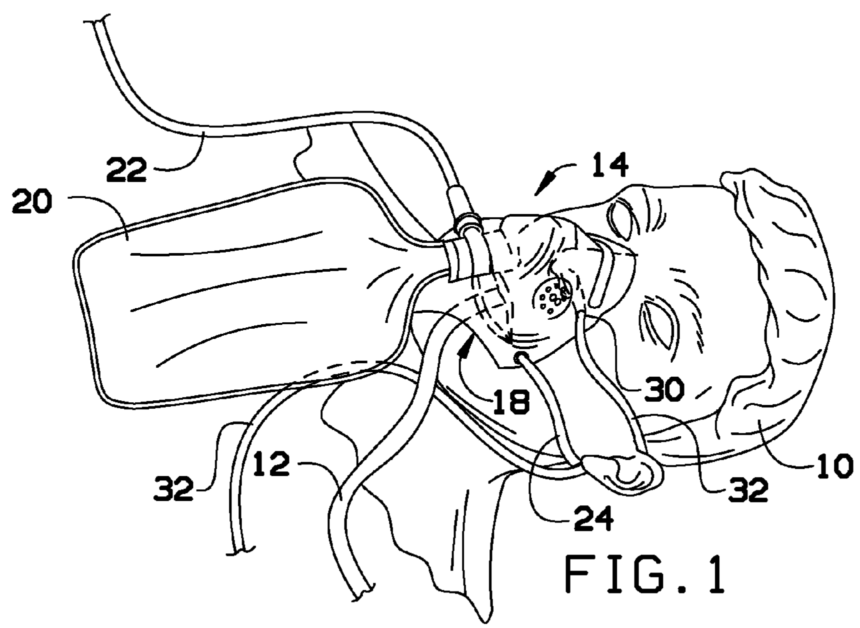
FIG. 1 is a perspective view of an oxygen face mask having an endoscopy tube side port and a nasal cannula slit, in use, according to an exemplary embodiment of the present invention.
Figure 2:
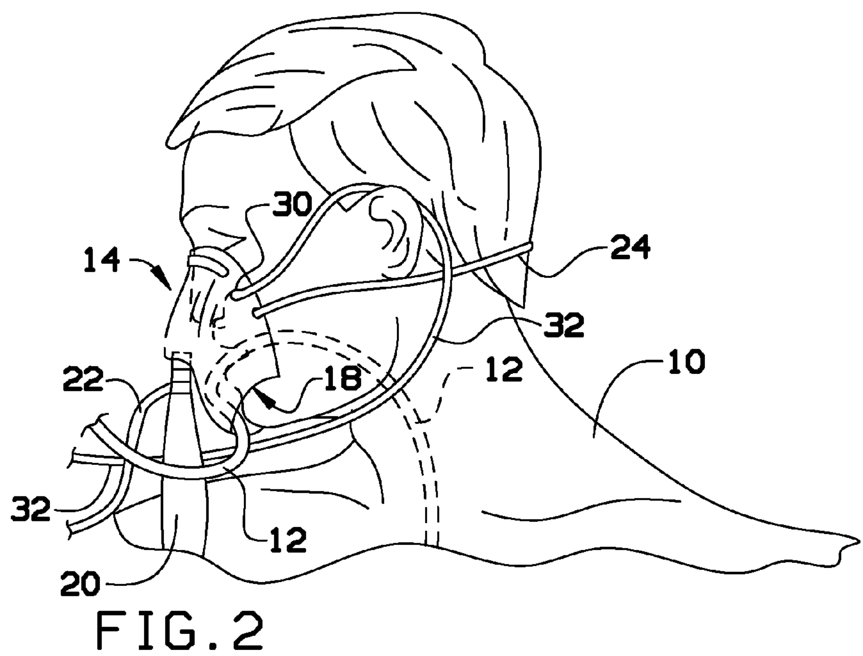
FIG. 2 is a side view of the oxygen face mask, in use, of FIG. 1.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a face mask that allows insertion of an upper endoscopy probe, a transesophageal echo probe for exams, or the like. Currently, a nasal cannula is used to measure carbon dioxide expired by the patient and deliver oxygen to sedated patients undergoing these procedures. Use of a face mask, such as a non-rebreathing face mask, during these procedures allows increased delivery of oxygen in patients with compromised respiratory function. A side port can be cut into the non-rebreathing face mask to allow insertion of the probes into patient's mouths while allowing delivery of a higher oxygen concentration.

Referring now to FIGS. 1 through 8, a patient 10 can wear a face mask 14 for receiving supplemental oxygen during a procedure, such as an endoscopy, wherein endoscopy tube 12 may be inserted into the mouth 26 of the patient 10.

The face mask 14 can include a side port 18 typically formed in a side of the face mask 14 at the chin end thereof. The side port 18 can allow the endoscopy tube 12 to pass while the face mask 14 is still disposed on the face of the patient 10. In some embodiments of the present invention, a flexible diaphragm can be disposed over the side port 18, allowing the endoscopy tube 12 to pass through while limiting the escape of oxygen from passing out through the side port 18.

The face mask 14 can be made in various designs. The face mask 14 can include an oxygen reservoir bag 20. An oxygen input tube 22 can provide a flow of oxygen into the face mask 14. The reservoir bag 20 can also receive oxygen from the oxygen input tube 22. The face mask 14 can be designed similar in operation to a non-rebreathing mask or a partial non-rebreathing mask.

The face mask 14 can include a strap 24 for holding the face mask 14 on the face of the patient 10. The strap 24 can extend through a strap hole 38 in the face mask 14, form a loop 34 and connect onto itself with, for example, a hook and loop fastener 36, such as Velcro. This can allow the strap 24 of the face mask 14 to be easily loosened and repositioned.

Figure 3:
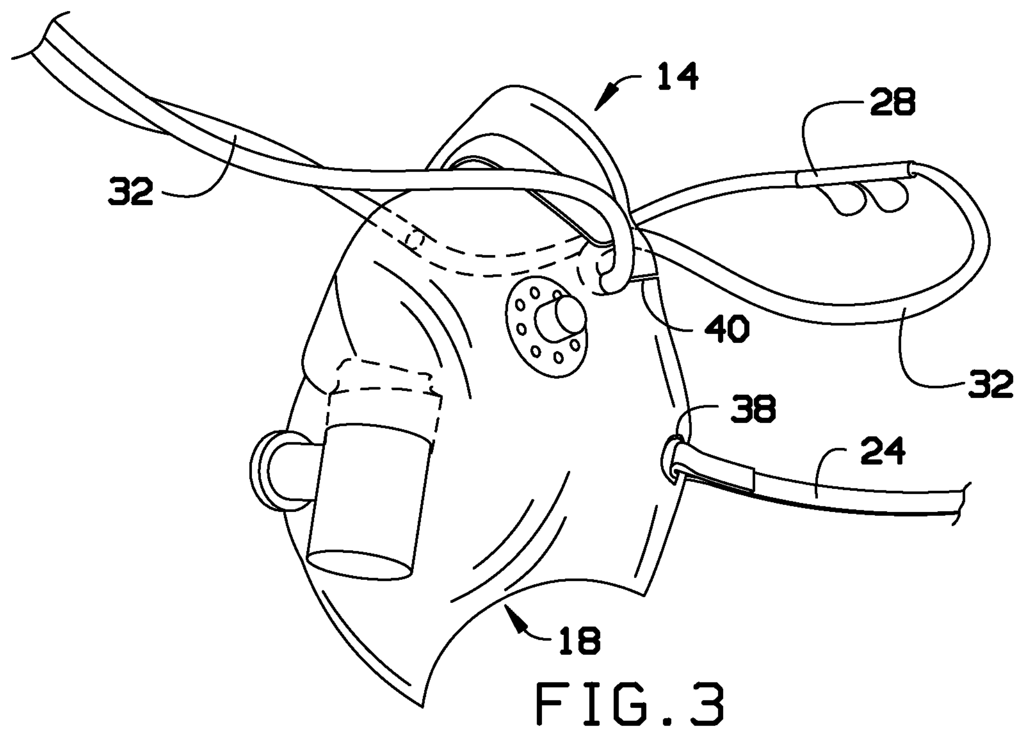
FIG. 3 is a perspective view of the oxygen face mask of FIG. 1.
Figure 4:
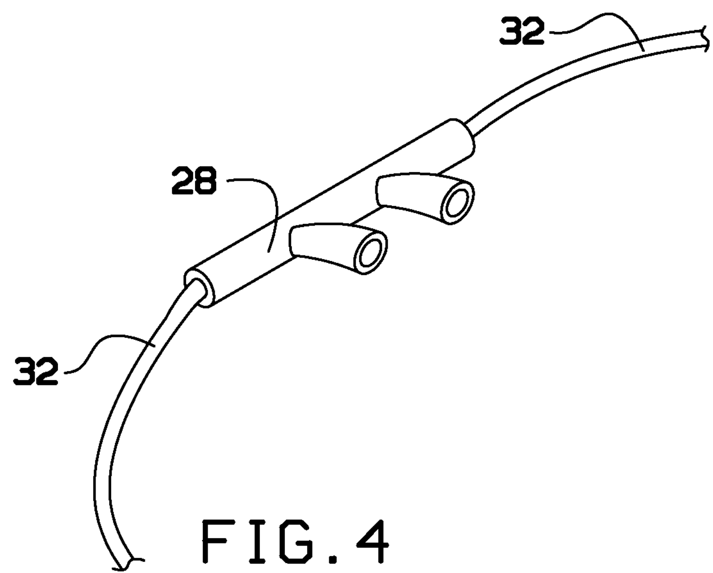
FIG. 4 is a perspective view of a nasal cannula used with the oxygen face mask of FIG. 1.
Figure 5:
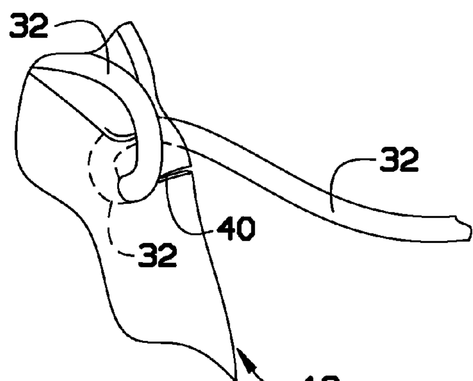
FIG. 5 is a detailed side view of the oxygen face mask of FIG. 1, showing a connection of the slit on the mask at the insertion site of the nasal cannula.
Figure 6:
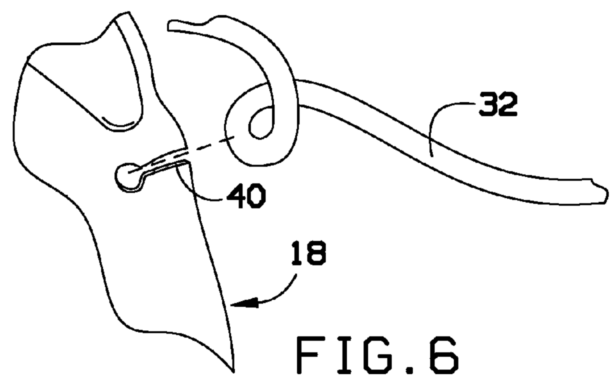
FIG. 6 is an exploded detailed side view of the oxygen face mask of FIG. 1 showing the slit on the face mask at the insertion site of the nasal cannula.
Figure 7:
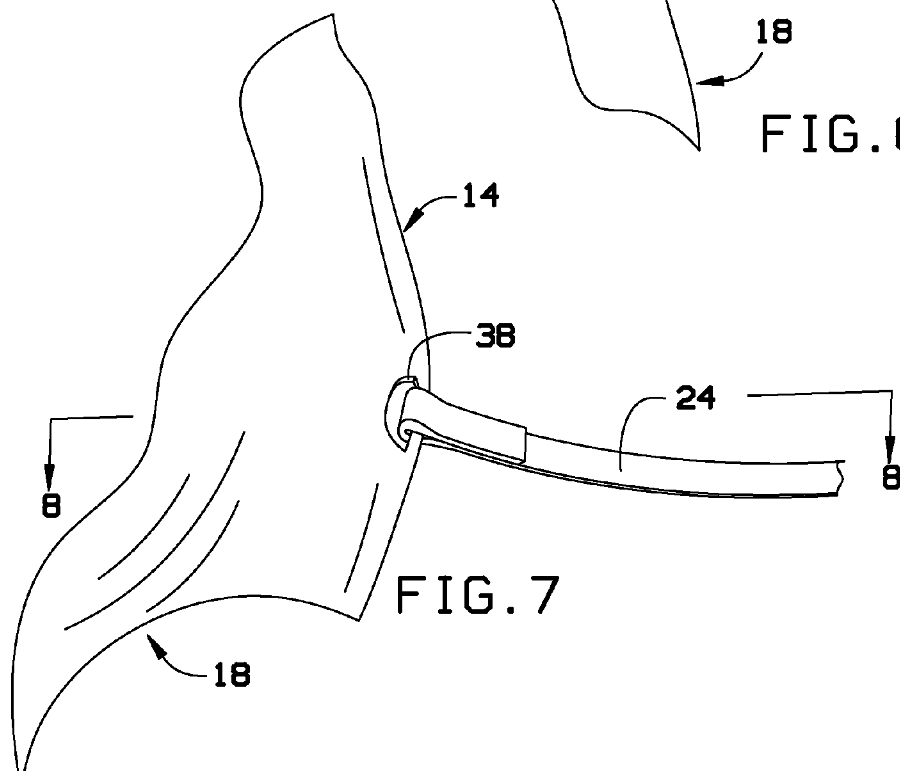
FIG. 7 is a detailed side view of the oxygen face mask of FIG. 1 showing a hook-and-loop strap on the face.
Figure 8:
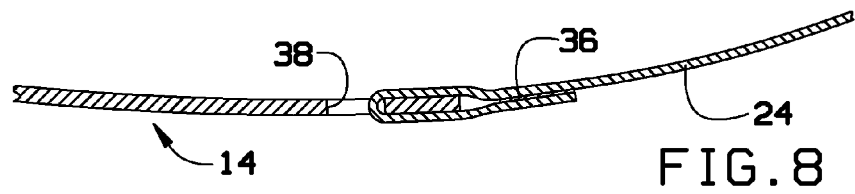
FIG. 8 is a cross-sectional view taken along line 8-8 of FIG. 7.

A nasal cannula 28 can include oxygen delivery and capnography tubes 32. These tubes 32 can be threaded through holes in the sides of the face mask 14 as shown in FIG. 3. The nasal cannula 28 can be used to deliver additional oxygen in addition to measure end-tidal carbon dioxide. The current standard of care for anesthesiologists is to measure end-tidal carbon dioxide when sedating patients for endoscopic procedures.

The nasal cannula tube 32 can fit into a slit 40 cut from sides of the face mask 14. The slits 40 can be, for example, keyhole shaped to hold the nasal cannula tube 32 in place while allowing for its removal if needed (or allowing the face mask 14 to be removed from the patient while keeping the nasal cannula 28 on the patient, for example).

The face mask 14 of the present invention can allow oxygen flow and concentration significantly higher than the conventional nasal cannula, while allowing an endoscopic tube to be inserted into the patient's mouth. The nasal cannula can allow delivery of additional oxygen as well as the ability to measure end-tidal carbon dioxide. The resulting face mask is a safe and effective oxygen delivery system for sedated patients, including those with compromised respiratory function.

The above described slit 40 at the nasal cannula insertion site and the hook and loop connection strap 24 on the face mask 14 allow for easy separation of the face mask 14 from the nasal cannula 28. Therefore, as a patient recovers from sedation and oxygen requirements drop, the face mask 14 can be removed from the patient for comfortable recovery with continued delivery of oxygen and monitoring of carbon dioxide through the nasal cannula 28.

It should be understood, of course, that the foregoing relates to exemplary embodiments of the invention and that modifications may be made without departing from the spirit and scope of the invention as set forth in the following claims.

What is claimed is:

1. An oxygen delivery device comprising:
- a face mask adapted to fit over a nose and mouth of a patient;
- a tube side port formed in an outer, face-contacting edge of the face mask such that the face mask only partially surrounds a tube passing through the tube side port; and
- a nasal cannula disposed in the face mask, the nasal cannula having prongs adapted to be disposed into the nose of the patient under the face mask, wherein
- the tube side port is formed so that the face mask is placeable over and liftable from the nose and mouth of the patient without requiring contact between the tube and any portion of the face mask and without disturbing the tube inserted through the tube side port; and
- the tube side port has a width that is widest at an outermost portion of the face mask.

2. The oxygen delivery device of claim 1, wherein the nasal cannula performs capnometry.

3. The oxygen delivery device of claim 1, further comprising a strap attached to each side of the face mask and operable to support the face mask on the patient.

4. The oxygen delivery device of claim 3, wherein the strap passes through strap holes in the face mask and connects to itself with a hook and loop fastener.

5. The oxygen delivery device of claim 1, further comprising an oxygen reservoir bag operable to release oxygen into the face mask.

6. The oxygen delivery device of claim 5, further comprising an oxygen input tube operable to deliver oxygen to the face mask and the oxygen reservoir bag.

7. The oxygen delivery device of claim 1, wherein an endoscopy tube fits into the tube side port while permitting the face mask to remain on the patient.

8. The oxygen delivery device of claim 1, further comprising slits cut from sides of the face mask, the slits permitting nasal cannula tubing to fit therein and removably attach to the face mask.

9. An oxygen delivery device comprising:
- a face mask adapted to fit over a nose and mouth of a patient;
- an oxygen reservoir bag operable to release oxygen into the face mask;
- a tube side port formed in an outer, face-contacting edge of the face mask such that the face mask only partially surrounds a tube passing through the tube side port;
- a nasal cannula disposed in the face mask, the nasal cannula having prongs adapted to be disposed into the nose of the patient under the face mask; and
- a strap passing through strap holes in each side of the face mask, the strap operable to support the face mask on the patient, the strap adjustably attaching to itself with a hook and loop fastener, wherein
- the tube side port is formed so that the face mask is placeable over and liftable from the nose and mouth of the patient without requiring contact between the tube and any portion of the face mask and without disturbing the tube inserted through the tube side port; and
- the tube side port has a width that is widest at an outermost portion of the face mask.

10. The oxygen delivery device of claim 9, further comprising an oxygen input tube operable to deliver oxygen to the face mask and the oxygen reservoir bag.

11. The oxygen delivery device of claim 9, wherein an endoscopy tube fits into the tube side port while permitting the face mask to remain on the patient.

12. An oxygen delivery device comprising:
- a face mask adapted to fit over a nose and mouth of a patient;
- an oxygen reservoir bag operable to release oxygen into the face mask;
- an oxygen input tube operable to deliver oxygen to the face mask and the oxygen reservoir bag;
- a tube side port formed in an outer, face-contacting edge of the face mask such that the face mask only partially surrounds an endoscopy tube passing through the tube side port, the tube side port allowing the endoscopy tube to be used in the patient while the face mask is disposed on the patient and the tube side port further allows the face mask to be placed over and lifted from the nose and the mouth of the patient without requiring contact between the tube and any portion of the face mask and without disturbing the endoscopy tube, wherein the tube side port has a width that is widest at an outermost portion of the face mask;
- a nasal cannula disposed in the face mask, the nasal cannula having prongs adapted to be disposed into the nose of the patient under the face mask; and
- a strap passing through strap holes in each side of the face mask, the strap operable to support the face mask on the patient, the strap adjustably attaching to itself with a hook and loop fastener.

* * * * *